United States Patent [19]

Galle et al.

[11] Patent Number: 4,601,859

[45] Date of Patent: Jul. 22, 1986

[54] SELECTIVE HYDROGENATION OF ALIPHATIC DINITRILES TO OMEGA-AMINONITRILES IN AMMONIA WITH SUPPORTED, FINELY DISPERSED RHODIUM-CONTAINING CATALYST

[75] Inventors: James E. Galle, Madison; Frank Mares, Whippany; Steven E. Diamond, Springfield; Jeffrey Corsi, Andover, all of N.J.; Francis J. Regina, Brooklyn, N.Y.

[73] Assignee: Allied Corporation, Morris Township, Morris County, N.J.

[21] Appl. No.: 607,037

[22] Filed: May 4, 1984

[51] Int. Cl.[4] ............................................. C07C 121/43
[52] U.S. Cl. .............................. 558/459; 260/239 B; 546/184; 548/579; 564/491; 564/492
[58] Field of Search ................................. 260/465.5 R

[56] References Cited

U.S. PATENT DOCUMENTS

| 2,208,598 | 7/1940 | Rigby | 260/464 |
|---|---|---|---|
| 3,880,928 | 4/1975 | Drake | 260/583 P |
| 4,362,671 | 12/1982 | Diamond et al. | 260/465.5 R |
| 4,383,940 | 5/1983 | Murtha et al. | 252/460 |
| 4,389,348 | 6/1983 | Diamond et al. | 260/465.5 R |

FOREIGN PATENT DOCUMENTS 0077911  5/1983  European Pat. Off. .

OTHER PUBLICATIONS

Freifelder, J.A.C.S., 82, (1960), pp. 2386–2389.
Montecatin: C.A., 78, (1973), 29279u.

*Primary Examiner*—Joseph Paul Brust
*Attorney, Agent, or Firm*—Richard C. Stewart, II; Gerhard H. Fuchs

[57] ABSTRACT

A dinitrile is hydrogenated to an omega-aminonitrile with hydrogen with a supported highly dispersed rhodium catalyst and only ammonia present. The catalyst is prepared by hydrolyzing a rhodium(III) halide or nitrate with strong aqueous base at elevated temperatures, drying the supported rhodium hydroxide at elevated temperatures and intimately contacting with hydrogen the dried product with hydrogen at 260°–360° C. High conversions, selectivity to aminonitrile and long catalyst service times and catalyst recyclability are achieved in the absence of an aprotic solvent.

25 Claims, No Drawings

SELECTIVE HYDROGENATION OF ALIPHATIC DINITRILES TO OMEGA-AMINONITRILES IN AMMONIA WITH SUPPORTED, FINELY DISPERSED RHODIUM-CONTAINING CATALYST

BACKGROUND OF THE INVENTION

The present invention relates to the selective hydrogenation of aliphatic nitriles such as adiponitrile to omega aminonitriles such as ε-aminocapronitrile, employing only ammonia with a catalyst containing finely dispersed rhodium on basic metal oxide supports.

Rhodium has found practical applications in hydrogenations. Rhodium metal itself, and inorganic rhodium oxides and salts supported on an inert support have been used in certain applications. Examples of processes employing such inert rhodium materials are contained in P. N. Rylander, *Catalytic Hydrogenation in Organic Synthesis* (N.Y. 1979).

U.S. Pat. No. 4,389,348 (S. E. Diamond et al.) discloses that rhodium-based catalysts selectively hydrogenate dinitriles to aminonitriles in the presence of an aprotic solvent for the dinitrile and ammonia. However, in Example 10 of the U.S. Patent, increased amounts of ammonia even in the presence of aprotic solvent such as THF completely prevented rhodiumcatalyzed hydrogenation of the dinitrile.

Y. Takagi et al., *Scientific Papers Institute Physical & Chemical Research (Japan)*, Vol. 61, No. 3, pp. 114–17 (1967) discloses processes for hydrogenating nitriles with unsupported rhodium catalysts. In particular, rhodium hydroxide prepared by adding various amounts of sodium hydroxide to a hot aqueous solution of rhodium chloride was used as a catalyst for the hydrogenation of adiponitrile. Table II of the reference indicates that increased amounts of sodium hydroxide as a further additive increased the yield of hexamethylenediamine, but eventually retard the reaction rate. Lithium hydroxide was a superior additive. The yields were in most cases lower than the 80% yield reported using rhodium oxide prepared by the fusion of rhodium chloride with sodium nitrate.

M. Freifelder et al., *J. Am Chem. Soc.*, vol. 82, pp. 2386–2389 (1960) employed 5% rhodium on alumina to hydrogenate aliphatic nitriles and especially 3-indoleacetonitrile. Ammonia was present to suppress production of secondary amines, but also reduced the catalytic activity of the rhodium. Ammonia is known to suppress secondary amine formation and reduce activity with other Group VIII metal catalysts.

U.S. Pat. Nos. 2,208,598 and 2,257,814, each to Rigby (Dupont 1940), and German Pat. Nos. 836,938 (1952), 848,654 (1952) and 954,416 (1956), all to BASF, disclose various catalytic processes directed to producing omegaaminonitriles from dinitriles employing miscellaneous catalysts including Raney nickel and iron, but not specifically any of the platinum group. See also U.S. Pat. No. 2,762,835 to Swerdloff (Celanese 1956).

Italian Pat. No. 845,999 to Montecatini Edison S.p.A. (1969) discloses the hydrogenation of dinitriles having one or two carbons shorter than adiponitrile (e.g. succinonitrile) in the presence of a rhodium catalyst and ammonia to produce an omega-aminonitrile.

None of these patents provides a process with high selectivity to aminonitrile (compared to by-products, e.g., diamine and secondary amine) at high conversions of dinitrile with high rates of catalyst turnover and long catalyst life in the presence of ammonia as the only solvent.

BRIEF DESCRIPTION OF THE INVENTION

It has been discovered that certain highly-dispersed inorganic rhodium materials catalyze the hydrogenation of dinitriles with high selectivity to omega-aminonitriles in the presence of high concentrations of ammonia while maintaining high rates of catalyst turnover and long catalyst life. Accordingly the present invention includes a process for producing an omega-aminonitrile which comprises reacting at a reaction temperature of between about 20° C. and about 200° C. a dinitrile of the formula $NC-(CH_2)_n-CN$, with n being an integer from 1 to 10, with hydrogen at a partial pressure of at least about one atmosphere in the presence of:

(a) ammonia in a molar amount at least equal to the molar amount of dinitrile present, and (b) a rhodium-containing catalyst prepared by hydrolyzing a rhodium halide or nitrate on a basic support selected from the group consisting of basic alumina, thoria, alkaline earth metal oxides and alkaline earth metal carbonates with strong aqueous base at a first temperature between about 50° C. and about 100° C. to produce a supported rhodium hydroxide, drying the supported rhodium hydroxide at subatmospheric pressure and a second temperature between about 50° C. and about 250° C., and intimately contacting the dried supported rhodium hydroxide with hydrogen at a third temperature between about 260° C. and about 360° C.; and recovering the omega-aminonitrile of the formula $NC-(CH_2)_n-CH_2NH_2$, as the major product.

DETAILED DESCRIPTION OF THE INVENTION

It was discovered that, by careful control of certain conditions chosen for preparation of the rhoduim on basic oxide catalyst disclosed by U.S. Pat. No. 4,389,349 as useful for selective hydrogenation of dinitriles into aminonitriles, there was produced a more highly dispersed rhodium on basic metal oxides catalyst which effected highly selective hydrogenation of dinitniles, such as adiponitrile, into aminonitriles, such as ε-aminocapronitrile, in pure ammonia. While the prior art taught ammonia was useful in supressing formation of by-products during hydrogenation of dinitriles by rhodium on magnesia, the prior art, e.g., U.S. Pat. No. 4,389,348 required the presence of susbtantial amounts of aprotic co-solvents to prevent deactivation of the rhodium-based catalyst. We have surprisingly discovered that highly dispersed rhodium on basic metal oxides prepared in accordance with the present invention operates in pure ammonia at high catalyst turnover rates and for extended lifetimes to effect the highly selective hydrogenation of dinitriles into amminotriles while minimizing production of less desireable by-products compared to rhodium-based catalyst of U.S. Pat. No. 4,389,348. In accordance with a preferred embodiment of the present invention, at high, i.e., 70% conversion, adiponitrile as a 10% (w/v) solution of adiponitrile in pure ammonia was hydrogenated at 100° C. and at a pressure of 1500 psig (10.2 MPa) into ε-aminocaprontrile with 94.1% selectivity; by-products 1,6-hexanediame, (compound 3) hexamethyleneimine (compound 4) and bis[5-cyanopentyl]amine (compound 5) were formed in 5, 0.5 and 0.4% selectivities, respectively. Thus, by operation in accordance with the process of the present invention, the selectivity to aminonitrite is higher, the amounts of less desirable by-products (compounds 4 and 5) are lower and the service lifetime of the catalyst longer compared to results acheived previously, e.g., as disclosed in U.S. Pat. No. 4,389,348. In addition, by using pure ammonia as solvent, instead of solvent mixtures of ammonia and aprotic solvents, such as tetrahydrofuran, as previously thought necessary, the operation of the process, especially on a continuous commercial scale, is simplied, i.e., the complexity of the solvent recycling trains is reduced.

The dinitrile used as reactant in the present process may be adiponitrile (wherein n is 4 in the above formula) or may be other similar dinitriles of 3–12 carbons, such that n can vary from 1 to 10. Adiponitrile is most preferred, with somewhat less preferred dinitriles including malononitrile, succinonitrile, glutaronitrile and pimelonitrile.

In the reaction mixture the dinitrile is dissolved only in ammonia. The presence in the reaction mixture of aprotic solvent such as tetrahydrofuran, dioxane, diglyme and similar ethers is not necessary. However, small amounts of aprotic solvent sufficient to dissolve the dinitrile may be tolerated without departing from the scope of the present invention.

Hydrogen is normally present as a gas at low to moderate pressure in contact with the solution of dinitrile, with some hydrogen dissolved in the solvent. Partial pressures of hydrogen of at least about one atmosphere, and preferably between about 5 and 100 atmospheres are preferred. The total pressure is equal to the sum of the partial pressure of ammonia and the partial pressure of hydrogen, at the reaction temperature. Raising the partial pressure of hydrogen not only increases the hydrogenation rate but also improves the selectivity to aminonitrile. The reaction temperature is suitably between about 20° C. and about 200° C., and is preferably between about 50° C. and about 150° C., and more preferably between about 80° C. and 120° C.

Ammonia is present during the reaction to inhibit the formation of by-products, and especially cyclic amine (e.g. azacycloheptane) and dimers (e.g., di(5-cyanopentyl)amine), both of which are formed from $\epsilon$-aminocapronitrile intermediate. Ammonia is present in molar amounts at least equal to the dinitrile, and preferably in a mole ratio of ammonia to dinitrile of about 5:1 to about 100:1, more preferably about 10:1 to about 50:1.

The rhodium-containing catalyst is one prepared by absorbing a rhodium substance on high surface area basic metal oxides, hydrolysis to the rhodium hydroxide, drying and reduction of a supported rhodium; with the conditions of all four preparative steps having an effect on catalyst performance. The rhodium nitrate or halide, e.g., $Rh(NO_3)_3$, $RhCl_3$, $RhBr_3$ or $RhI_3$, but preferably $RhCl_3$, is adsorbed on a basic support. Magnesium oxide (magnesia) is the preferred support, but other alkaline earth oxides (e.g. CaO, BaO, SrO) and mixtures thereof, e.g., MgO/CaO may be used, as may the corresponding alkaline earth carbonates. Thoria (which is inherently basic) and basic alumina, that is alumina rendered basic by treatment with strong bases such as alkali metal hydroxide, or basic rare earth metal oxides, e.g., those of Yb, Eu and Sm may also be used. While the water or hydroxyl content and surface area of the support are not critical, basic metal oxides, for example, magnesias of high surface area from 150 to 300 $m^2/g$ surface area are especially suitable. Treatments to reduce the hydroxyl content and increase the surface area, e.g., by calcining, are preferably performed on the support before adsorbing the rhodium nitrate or halide thereby obtaining only monomolecular coatings, i.e., substantially free of aggregates.

The supported rhodium halide is hydrolyzed with strong aqueous base at a first elevated temperatures (e.g. 50°–100° C.). While the base is preferably an alkali metal hydroxide (e.g. NaOH, KOH or LiOH), it may also be a quaternary ammonium hydroxide or other strong soluble base. The stoichiometric amount of base (3:1) or a slight excess is preferably used, since less base will leave halide on the catalyst and a larger excess serves no useful purpose. The product of hydrolysis is a supported rhodium hydroxide.

The supported rhodium hydroxide is preferably washed (with water) before drying. A preferred procedure is for at least the final water rinse to be at elevated temperatures such as 50°–100° C.

The supported rhodium hydroxide is then dried, in one or more steps, with at least one stage being at subatmospheric pressure and a second elevated temperature (e.g. about 50°–250° C., preferably about 80°–150° C., more preferably about 100° C.). The dried product, which may be part hydroxide and part oxide, or may be substantially all oxide, is then intimately contacted with hydrogen at elevated temperature prior to introduction of the dinitrile. It is critical that the third temperatures for hydrogenation of the dried product be maintained between about 260° C. and 360° C., preferably between about 290° C. and 310° C.; even slightly lower third temperatures, e.g., 250° C. produced inactive catalyst and slightly higher third temperatures, e.g., 400° C. produced only weakly active or inactive catalyst. For third temperature at the lower end of the range, e.g., 260°–280° C., longer reaction times should be used for the reduction; for third temperatures at the higher end of the range, e.g., 320° C.–360° C., shorter reaction times should be used so as to avoid the formation of three-dimensional rhodium aggretates. Hydrogen may be at atmospheric pressure at this stage or may be at a superatmospheric pressure.

It is critical that the supported catalyst remain in intimate contact with the hydrogen during the calcination/hydrogenation step. The use of a rotating reduction tube was a convenient method of agitation, although not the exclusive method to achieve intimate contact. A comparison of the results of Example 3 [rhodium on magnesia catalyst prepared by hydrogenation (no agitation) at 300° C.] with those of Examples 5 and 6 (rhodium on magnesia catalyst prepared by intimate contact of hydrogen at 300° C.) dramatically illustrates the criticality of agitation.

From examination of a transmission electron micrograph of highly dispersed 5% rhodium on magnesia catalyst (BET surface area of 101 $m^2/g$) prepared in accordance with the present invention (see Example 4), it is evident that the rhodium is in fact ultra-dispersed on the magnesia; the rhodium was present as two dimensional rafts of about 1.8 nm in size, corresponding to about 12 rhodium atoms per raft. Chemisorption experiments confirmed this interpretation of the transmission electron micrograph; hydrogen uptake of about 0.7 atoms of H per atom of Rh was observed as expected for rhodium rafts of this size (see D. J. C. Yates et al., J. Catal., 1979, Vol. 57 at page 41.)

In contrast, the rhodium on magnesia catalyst prepared by calcination and hydrogenation even with agitation at 400° C. was observed to be only a weakly active catalyst for hydrogenation of dinitrile; See Example 8. From examination of a transmission electron micrograph of the weekly active 5% rhodium on magnesia prepared by hydrogenation at 400° C. with agitation, it is evident that the rhodium had aggregated into larger three-dimensional particles of 3 to 10 nm size (500-to 17,000 rhodium atoms per particle) size. It is believed that the highly dispersed rhodium on magnesia is responsible for the high selectivity and high catalytic activity in the process of the present invention. Surprisingly, the degree of dispersion of rhodium on the support is more critical than the surface area of the support or of the supported catalyst. Thus, while even a slight variation in the third temperature or lack of agitation produced an inactive or weakly active catalyst, highly dispersed rhodium-containing catalysts of medium surface area (about 75 to 125 $m^2/g$ see Runs #I-VII of Table 1) were excellent catalysts and other less highly dispersed rhodium-containing catalyst of higher surface area (>200 $m^2/g$) exhibited poor catalytic properties (See Comparative Example 7).

The reaction temperature for hydrogenation of the dinitrile may be about 20° C. to about 200° C., and is preferably about 50°–150° C. and more preferably about 80°–120° C. The hydrogen partial pressure is at least one atmosphere, with increasing partial hydrogen pressures causing greater reaction rates. The total reaction pressure is the sum of the partial pressures of hydrogen and ammonia; the partial pressure of dinitriles and aminonitriles at the reaction temperatures of the present invention are insignificant. Moderate total pressures of 1.4–3.4 MPa (200–500 psig) or high pressures of 10.2 MPa (1500 psig) or higher are conveniently used.

The process of the present invention may be operated batchwise or continously; in the continuous mode of operation, the rhodium on magnesia catalyst may be conveniently placed in a flow reactor.

The reaction times are not critical, with contact times of minutes or hours being generally suitable. With a suitable catalyst, excessive times (determined by routine experiment, but frequently over four hours) will cause greater amounts of hydrogenation of the desired aminonitrile product to the undesired diamine by-product. A suitable range of reaction times are available whereat the dinitrile conversion is high, e.g., about 70%, but the by-product diamine is still low.

Examples 1-3 and 7 and 8 are Comparative Examples illustrating the preparation and use of the rhodium on magnesia catalyst of U.S. Pat. No. 4,389,348.

EXAMPLE 1

The preparation of the supported rhodium on magnesia catalyst is illustrated below for the 2% by weight rhodium catalyst. Commercially available magnesia (Harshaw Chemical Company, ⅛" tablets) was ground and sieved. Only the 80-100 mesh fraction was utilized.

299.5 mg of rhodium trichloride trihydrate ($RhCl_3 \cdot 3H_2O$) was dissolved in a minimum amount of water (approximately 2 mL). 5983.8 mg of the magnesia was formed into a thin paste by the addition of water. This paste was then added to the rhodium solution with constant stirring. This mixture was stirred overnight to allow the rhodium to adsorb onto the magnesia support. The originally white magnesia was now beige in color. The solid was dried in a vacuum oven at approximately 100° C. overnight.

3519.3 mg of this supported rhodium trichloride on magnesia were added to a round bottom flask. To this solid was added a slight excess of a 10% aqueous solution of sodium hydroxide. This suspension was heated to 90° C. for approximately 3 hours. At the end of this time the solid was filtered, washed with copious amounts of water (in some of these examples the water used was at 90° C., in others only room temperature water was used) until the pH of the filtrate was neutral and then placed in a vacuum oven at approximately 100° C. overnight. The resulting rhodium hydroxide on magnesia is yellow in color.

Prior to reaction the rhodium hydroxide on magnesia was reduced by hydrogen in a vertical tube having a glass frit on the bottom and inserted into a furnace at 300° C. for approximately 1 hour. The vertical tube was not rotated or agitated in any way during the reduction by hydrogen.

252.8 mg of this rhodium on magnesia catalyst (2%) were added to a stainless steel reactor equipped with a glass liner and magnetic stir bar. 3180.4 mg of adiponitrile and 15 mL of tetrahydrofuran were then added. Approximately 5.4 g of ammonia were then distilled into the autoclave at which time it was sealed and pressurized to approximately 500 psi (3.4 MPa) with hydrogen gas. The autoclave was heated to 100° C. overnight with constant stirring. At this time the autoclave was vented, opened, and the catalyst was filtered. The filtrate was analyzed by standard gas chromatographic techniques to yield epsilon aminocapronitrile as the major product. The conversion of adiponitrile was 74% with a selectivity to epsilon-aminocapronitrile of 93%. The ratio of epsilonaminocapronitrile to 1,6-hexanediamine was approximately 18.

Examples 2 and 3 employed a 5% by weight rhodium on magnesia catalyst prepared in an analagous manner to that described in Example 1.

EXAMPLE 2

Example 1 was repeated with 254.8 mg of 5% by weight rhodium on magnesia catalyst, 3171.0 mg of adiponitrile, 15 mL of tetrahydrofuran and approximately 5.3 g of ammonia. After approximately 4 hours of heating at 100° C. (hydrogen pressure was 500 psi (3.4 MPa) the autoclave was vented, opened, and analyzed by standard gas chromatographic techniques. The conversion of adiponitrile was 86% with a selectivity to ε-aminocapronitrile of 87%. The ratio of ε-aminocapronitrile to 1,6-hexanediamine was approximately 8.9.

EXAMPLE 3

Example 1 was repeated with 255.2 mg of 5% by weight rhodium on magnesia catalyst, 3166.7 mg of adiponitrile, 10 mL of tetahydrofuran, and approximately 10 g of ammonia. After approximately 2 hours of heating at 100° C. and at a hydrogen pressure of 500 psi (3.4 mPa) no uptake of hydrogen gas was observed.

EXAMPLE 4

This Example illustrate the best mode of preparation of supported rhodium on magnesia catalyst for the process of the present invention.

Commercially available magnesia (Harshaw Chemical Co., ⅛" tablets) was ground and sieved; only the >80 mesh fraction was utilized. This ground magnesia was slurried in water (1 g of MgO/10 mL of $H_2O$) and heated in an oil bath at 90° C. for 3 hrs. This material was calcined at 400° C. for 24 hrs. in a static oven to give MgO (BET surface area 122 m²/g). To a round bottom flask, 2.2.g of this high surface area magnesia were added, with constant stirring, to a solution of 286 mg of rhodium trichloride trihydrate (RhCl₃·3H₂O) in 20 mL of distilled water. The red aqueous RhCl₃ solution in contact with the magnesia suspension decolorized rapidly and was colorless within one hour, indicating complete rhodium adsorption. The water was removed (rotating evaporation at 40° C.) and the resulting solid was dried overnight. A solution of 0.1 N NaOH (3.75 mL) was added to the above formed suspension. This suspension was heated at 90°-95° C. for 3 hrs. At the end of this time, the solid was filtered and washed with 2×10 mL portions of distilled water. The resulting solid was placed in vacuum oven at about 100° C. overnight. The resulting rhodium hydroxide on magnesia was yellow beige in color. The yellow-beige material was heated in 60 mL of water for 3 hrs. After filtration, the resulting solid was stored overnight in a vacuum oven at 100° C.

Prior to use in the reaction detailed in Example 5 below, the rhodium hydroxide on magnesia was reduced in a muffle furnace equipped with a Omega 400z kc thermocontroller and preheated to 300° C. To a glass tube (19 cm long×22 mm in diameter) were added 400 mg of rhodium (III) hydroxide on magnesia. The inlet side of the tube was connected to a compressed air driven reciprocating motor having a 300° arc (obtained from Aldrich Chemical Co.). The exit tube was connected to an oil bubbler. The tube was flushed with hydrogen for 15 min. While the hydrogen flow was continued, the exit end of the tube was stoppered and the tube was quickly inserted into the muffle furnace. The exit of the tube was connected to a bubbler; a hydrogen flow of 2-3 bubbles/second was maintained throughout the reaction. The entire assembly was titled 5°-10° from the horizontal so that exit of the reactor was higher than the entrance. The reciprocating motor was turned on and adjusted to about one arc/second. After one hour at 300° C.±10° C., the exit of the tube was stoppered and removed from the furnace. The catalyst was emptied from tube in an inert atmosphere glovebox (weight loss after calcination was about 25%). The resultant Rh/MgO is sufficiently pyrophoric to ignite hydrogen if emptied in air.

Examination of this catalyst by transmission electron microscopy showed the rhodium to be ultra dispersed.

EXAMPLE 5

In a mechanically stirred hydrogenation vessel were placed 11.565 g of adiponitrile, 4.871 g triethylene glycol dimethyl ether (internal standard), 200 mg of 5% rhodium on magnesia (prepared as described in Example 4) and 100 mL of anhydrous ammonia. The vessel was pressurized with 100 psig of hydrogen and heated to 100° C. As soon as the temperature reached 100° C., sufficient additional hydrogen was added to bring the total pressure to 1500 psig. The temperature was maintained at 100° C. and the pressure at 1450 to 1500 psig throughout the reaction. Samples were periodically withdrawn from the reactor and analyzed by gas chromatography. The total reaction time was 2 hrs. Plots of conversion versus selectivity to the products were made to greater than 70% conversion and the selectivity at 70% conversion was extrapolated from this plot. The results of this experiment is presented in Table 1, Run #VII (below). Runs #I-VI of Table 1 were obtained in a similar manner. The ratio of epsilonaminocapronitrile to 1,6-hexanediamine can be calculated from the selectivities reported in Table 1.

EXAMPLE 6

The reaction was carried out as in Example 5 using 10.0 g of succinonitrile as the substrate. After 5 ½ hours reaction time at 100° C. and 1000 psig total pressure, the product mixture was analyzed by gas chromatography; the analysis showed 89.4% conversion of the succinonitrile and 87.3% selectivity to 4-aminobutyronitrile.

TABLE 1

The Reduction of Adiponitrile Using Ammonia as Solvent in the Presence of Rhodium on Magnesia[1]

| Run # | Temp (°C.) | Total Pressure (psig) | Selectivities (%)[b] | | | |
|---|---|---|---|---|---|---|
| | | | 2[c] | 3[d] | 4[e] | 5[f] |
| I | 110 | 1100 | 87.5 | 4.8 | 2.2 | 5.3 |
| II | 110 | 1000 | 89.9 | 6.5 | 1.3 | 2.6 |
| III | 100 | 910 | 86 | 6.4 | 2.9 | 4.9 |
| IV | 90 | 1000 | 89.0 | 6.0 | 2.6 | 4.5 |
| V | 100 | 960 | 90.2 | 6.6 | 1.2 | 1.7 |
| VI | 95 | 960 | 86.2 | 8.1 | 1.7 | 3.7 |
| VII | 100 | 1500 | 94.1 | 5.0 | 0.5 | 0.3 |

Footnotes to Table 1
[1]Rhodium on magnesia catalyst was prepared in manner analogous to that described in Example 4. The BET surface areas for catalyst used in Runs #I-VII was about 75-125 m²/g.
[a]Partial pressure of NH₃ at 100° C. is estimated to be about 850 psig. The partial pressure of H₂ is estimated to be total pressure-850 psig.
[b]The selectivities were adjusted to 70% conversion (graphically). The error in the selectivity of 2 is estimated to be ±1%.
[c]2 = H₂H—(CH₂)₅—CN
[d]3 = H₂N—(CH₂)₆—NH₂

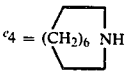
[e]4 = (CH₂)₆ NH

[f]5 = bis-[5-cyanopentyl]amine, [NC—(CH₂)₅—]₂NH

TABLE 2

Hydrogenation of Dinitriles Using Ammonia as Solvent in Presence of Rhodium on Magnesia

| Run # | Dinitrile | Conv.[1] (%) | Selectivities (%)[1,2] | | | |
|---|---|---|---|---|---|---|
| | | | 11[a-c] | 12[a-c] | 13[a-c] | 14[a-c] |
| VIII | Succinonitrile | 86.5 | 81.6 | 0 | 0 | 18.4 |
| IX | " | 85.5 | 85.5 | 0 | 0 | 14.5 |
| X | " | 89.4 | 87.3 | 0 | 0 | 13.3 |
| XI | Glutaronitrile | 60.9 | 92.9 | 1.0 | 0 | 3.9 |
| XII | " | 92.0 | 81.6 | 4.1 | 0.2 | 12.9 |
| XIII | Dicyanopentane | 73.9 | 82.2 | 0 | 17.7 | 0 |
| XIV | " | 92.7 | 65.4 | 0 | 34.0 | 0 |

[1]Conversions and selectivities are based on gc area percentages by assuming that all compounds have equal response facors.
[2]11[a] H₂N(CH₂)₃—CN
11[b] H₂N(CH₂)₄—CN
11[c] H₂N(CH₂)₅—CN

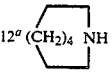
12[a] (CH₂)₄ NH

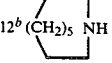
12[b] (CH₂)₅ NH

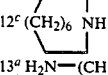
12[c] (CH₂)₆ NH

13[a] H₂N—(CH₂)₄—NH₂
13[b] H₂N—(CH₂)₅—NH₂
13[c] H₂N—(CH₂)₆—NH₂
14[a-c] various dimeric products

COMPARATIVE EXAMPLE 7

This Example illustrates that less-highly dispersed rhodium on magnesia catalyst having high surface area and prepared by hydrogenation at 275°, without agitation, exhibited poor catalytic properties for reduction of adiponitrile to 6-aminocapronitrile.

The procedure of Example 1 was followed to prepare a rhodium (III) hydroxide on magnesia except that the suspension of rhodium trichloride on magnesia in aqueous sodium hydroxide was stirred at 95° C. for 18 hrs. The resulting reaction mixture was filtered, and the resultant solid was washed with water. The solid rhodium hydroxide on magnesia was suspended in 200 mL of water heated at 95° C. for 70 hrs. After filtration and washing (water), the material was dried in a vacuum oven at 100° C. (0.1 torr) for 1 hr.; the rhodium hydroxide on magnesia material (14.65 g) was stored in a dry box.

A 1 g sample of rhodium hydroxide on magnesia was calcined in air at 400° C. for 18 hrs. to provide 0.68 g of material having a BET surface area of 294.4 m$^2$/g (N$_2$). This high surface area material was placed in a vertical glass tube with a bottom glass frit in a slow flow of hydrogen. Under a constant hydrogen flow, the vertical tube was placed in an oil bath raised to a temperature of 250° C. over 45 minutes. After 25 minutes at 250° C., the temperature was raised to 275° C. and reduction was continued at 275° C. for 95 minutes. The tube was not agitated or rotated during the reduction. The reduced rhodium on magnesia was removed from the bath and stored in an inert atmosphere dry box. The BET surface area of the reduced rhodium on magnesium was 297.8 m$^2$/g.

The reduction of 2.10 g of adiponitrile in 10 mL of tetrahydrofuran (THF) and 5.9 mL (78° C.) of ammonia and 90 mg of triglyme in the presence of 40 mg of the above prepared rhodium on magnesia was performed in a Parr autoclave at 98°–$\phi$° C. with constant stirring. Samples were removed at intervals and analyzed by gas liquid chromatography. The results are summarized in Table 3.

TABLE 3

Reduction of Adiponitrile in THF/NH$_3$ at 100° C. with High Surface Area Rhodium on Magnesia Catalyst of Example 7.

| Time (min) | Temp. (°C.) | Total Pressure (psig) | C$^1$ (%) | S$^2$ (%) |
|---|---|---|---|---|
| 0 | — | | —$^3$ | —$^3$ |
| 10 | 98 | 792 | —$^3$ | —$^3$ |
| 105 | 99 | | 28.6 | 97.4 |
| 195 | 100 | 771 | 41.7 | 95.1 |
| 250 | 99 | 763 | 48.1 | 92.8 |

FOOTNOTES TO TABLE 3
$^1$% Conversion of adiponitrile.
$^2$% Selectivity to 6-aminocapronitrile.
$^3$Not determined.

This Example illustrates that the high surface area rhodium on magnesia catalyst reduced, without agitation at 275° C. exhibited poor catalytic activity; the rate of reaction as measured by percent conversion slowed down considerably after 90 minutes and was eventually stopped. Our experimental data suggests that if the rhodium on magnesia catalysts for the selective hydrogenation of dinitriles to aminonitriles exhibit no or low activity in an ammonia/tetrahydrofuran (THF) solvent mixture, such rhodium on magnesia catalysts are less active or completely inactive in the selective hydrogenation reaction wherein only ammonia is present, i.e, in the absence of an aprotic solvent such as THF. As can be seen from comparison of the results of Table 3 with the results summarized in Table 1, the moderate surface area catalyst (of Example 4) prepared in accordance with the present invention exhibited higher conversions (in excess of 70%) and comparable selectivities in pure ammonia. It is expected that the catalytic activity of the catalyst of Example 7 for the reduction of adiponitrile in ammonia (in the absence of an aprotic solvent such as THF) would be similar to that reported for catalyst used in Example 3.

COMPARATIVE EXAMPLE 8

The procedure of Example 4 was followed except that a temperature of 400° C. was used in the reduction/calcination step which was performed with rotation of the tube in the furnace.

It is believed that were the material of this Example to be used to reduce adiponitrile in accordance with the procedure of Example 5, it would be only weakly active catalyst, i.e., very low conversions of adiponitrile would be observed compared to results reported in Table 1 for the catalyst prepared in accordance with the present invention.

The above-detailed Examples are illustrative of the present invention. Other modifications such as use of basic supports such as basic alumina, basic thoria and other alkaline earth metal oxides and alkaline earth metal carbonates are expected to produce similar results to those summarized in Tables 1 and 2.

What is claimed is:

1. A process for producing an omega-aminonitrile which comprises reacting at a reaction temperature of between about 20° and about 200° C. a dinitrile of the formula NC—(CH$_2$)$_n$—CN with n being an integer from 1 to 10 with hydrogen at a partial pressure of at least about one atmosphere in the presence of:
(a) ammonia in a molar amount at least equal to the molar amount of dinitrile present, and
(b) a rhodium-containing catalyst prepared by hydrolyzing a rhodium (III) halide or nitrate on a basic support selected from the group consisting of basic alumina, thoria, alkaline earth metal oxides and alkaline earth metal carbonates with strong aqueous base at a first temperature between about 50° C. and about 100° C. to produce a supported rhodium (III) hydroxide, drying the supported rhodium hydroxide at subatmospheric pressure and a second temperature between about 50° C. and about 250° C., and intimately contacting with agitation the dried rhodium hydroxide with hydrogen at a third temperature between about 260° and about 360° C. for a period of time necessary to reduce the rhodium (III) hydroxide to rhodium and to preserve an ultra-dispersion of the rhodium characterized in that two-dimensional rafts are present; and recovering the omega-aminonitrile of the formula NC—(CH$_2$)$_n$—CH$_2$—NH$_2$, as the major product.

2. The process of claim 1 wherein ammonia is present at a molar ratio to dinitrile between about 5:1 and about 15:1.

3. The process of claim 1 wherein ammonia is present at a molar ratio to dinitrile between at least 10:1.

4. The process of claim 1 wherein said second reaction temperature is between about 50 and about 150° C.

5. The process of claim 1 wherein the partial pressure of hydrogen is at least one atmosphere.

6. The process of claim 1 wherein said basic support is magnesium oxide.

7. The process of claim 1 wherein n is 4.

8. The process of claim 1 wherein the reacting is conducted in absence of an aprotic solvent.

9. The process of claim 1 wherein the third temperature is between about 290° and about 310° C.

10. The process of claim 1 wherein the reaction to produce an omega-aminonitrile is carried out in the presence of aprotic solvent, characterized in that an amount of said solvent does not exceed that which is sufficient to dissolve the dinitrile reactant.

11. The process of claim 1 wherein said rhodium (III) halide or nitrate is selected from the group consisting of $Rh(NO_3)_3$, $RhI_3$, $RhBr_3$ and $RhCl_3$.

12. The process of claim 11 wherein said rhodium-containing catalyst is prepared from $RhCl_3$.

13. The process of claim 1 wherein said strong aqueous base is an inorganic base.

14. The process of claim 13 wherein said strong aqueous inorganic base is selected from the group consisting of alkali metal hydroxides an ammonium hydroxide.

15. The process of claim 12 wherein said base is an alkali metal hydroxide.

16. The process of claim 15 wherein said base is selected from the group consisting of sodium hydroxide, potassium hydroxide or lithium hydroxide.

17. A process for producing an omega-aminonitrile which comprises:

reacting at a reaction temperature of between about 20° C. and about 200° C. a dinitrile of the formula $NC-(CH_2)_n-CN$ with n being an integer from 1 to 10 with hydrogen at a partial pressure of at least about one atmosphere in the presence of an aprotic solvent in an amount not to exceed that which is sufficient to dissolve the dinitrile, and in the presence of ammonia in a molar amount at least equal to the molar amount of dinitrile present, and in the pressure of a rhodium-containing catalyst prepared by hydrolyzing a rhodium (III) compound selected from the group consisting of $Rh(NO_3)_3$, $RhCl_3$, $RhBr_3$ and $RhI_3$ on a basic support selected from the group consisting of basic alumina, thoria, alkaline earth metal oxides and alkaline earth metal carbonates with strong aqueous base selected from the group consisting of alkali metal hydroxides and ammonium hydroxide at a first temperature between about 50° C. and about 100° C. to produce a supported rhodium (III) hydroxide;

drying the supported rhodium hydroxide at subatmospheric pressure and a second temperature between about 50° C. and about 250° C.;

intimately contacting with agitation the dried rhodium hydroxide with hydrogen at a third temperature between about 260° C. and about 360° C. for a period of time necessary to reduce the rhodium (III) hydroxide to rhodium and to preserve an ultra-dispersion of the rodium characterized in that two-dimensional rafts are present; and recovering the omega-aminonitrile of the formula $NC-(CH_2)_n-CH_2-NH_2$, as the major product.

18. The process of claim 17 wherein said rhodium (III) compound is $RhCl_3$.

19. The process of claim 17 wherein said base is selected from the group consisting of alkali metal hydroxides.

20. The process of claim 19 wherein said base is selected from the groups consisting of lithium hydroxide, sodium hydroxide and postassium hydroxide.

21. The process of claim 19 wherein said third temperature is between about 290° C. and 310° C.

22. A process for producing an omega-aminonitrile which comprises reacting at a reaction temperature of between about 20° and about 200° C. a dinitrile of the formula $NC-(CH_2)_n-CN$ with n being an integer from 1 to 10 with hydrogen at a partial pressure of at least about one atmosphere in the absence aprotic solvent and in the presence of:

(a) ammonia in a molar amount at least equal to the molar amount of dinitrile present (b) a rhodium-containing catalyst prepared by hydrolyzing $RhCl_3$ on a magnesium oxide support with strong aqueous base selected from the group consisting of lithium hydroxide, sodium hydroxide and potassium hydroxide at a first temperature between about 50° C. and about 100° C. to produce a supported rhodium (III) hydroxide, drying the support rhodium (III) hydroxide at subatmospheric pressure and a second temperature between about 50° C. and about 150° C., and intimately contacting by agitation the dried rhodium (III) hydroxide with hydrogen at a third temperature between about 290° and about 310° C. for a period of time necessary to reduce the rhodium (III) hydroxide to rhodium and to preserve an ultra-dispersion of the rhodium characterized in that two dimensional rafts are present; and recovering the omega-aminonitrile of the formula $NC-(CH_2)_n-CH_2-NH_2$, as the major product.

23. The process of claim 1 wherein the intimate contacting by agitation of the supported rhodium (III) hydroxide with hydrogen in the reduction step is accomplished by rotation of a container supporting said rhodium hydroxide.

24. The process of claim 17 wherein the intimate contacting by agitation of the supported rhodium (III) hydroxide with hydrogen in the reduction step is accomplished by rotation of a container supporting said rhodium hydroxide.

25. The process of claim 22 wherein the intimate contacting by agitation of the supported rhodium (III) hydroxide with hydrogen in the reduction step is accomplished by rotation of a container supporting said rhodium hydroxide.

* * * * *